United States Patent
Yoshimura

(10) Patent No.: US 10,144,695 B2
(45) Date of Patent: Dec. 4, 2018

(54) METAL SOAP AND MANUFACTURING METHOD THEREFOR

(71) Applicant: NOF CORPORATION, Tokyo (JP)

(72) Inventor: Takeshi Yoshimura, Hyogo (JP)

(73) Assignee: NOF CORPORATION, Tokyo (JP)

( * ) Notice: Subject to any disclaimer, the term of this patent is extended or adjusted under 35 U.S.C. 154(b) by 0 days.

(21) Appl. No.: 15/551,510

(22) PCT Filed: Feb. 9, 2016

(86) PCT No.: PCT/JP2016/053804
§ 371 (c)(1),
(2) Date: Aug. 16, 2017

(87) PCT Pub. No.: WO2016/132967
PCT Pub. Date: Aug. 25, 2016

(65) Prior Publication Data
US 2018/0093938 A1    Apr. 5, 2018

(30) Foreign Application Priority Data
Feb. 17, 2015   (JP) ................. 2015-028558

(51) Int. Cl.
| | | |
|---|---|---|
| A61K 8/36 | (2006.01) | |
| A61Q 1/12 | (2006.01) | |
| C07C 53/126 | (2006.01) | |
| C07C 51/41 | (2006.01) | |
| A61K 8/02 | (2006.01) | |

(52) U.S. Cl.
CPC .............. *C07C 51/41* (2013.01); *A61K 8/022* (2013.01); *A61K 8/0241* (2013.01); *A61K 8/36* (2013.01); *A61K 8/361* (2013.01); *A61Q 1/12* (2013.01); *C07C 53/126* (2013.01); *A61K 2800/412* (2013.01); *A61K 2800/622* (2013.01); *A61K 2800/651* (2013.01)

(58) Field of Classification Search
CPC .................................. C07C 51/41; A61K 8/36
USPC .......................................................... 554/158
See application file for complete search history.

(56) References Cited

U.S. PATENT DOCUMENTS

| | | |
|---|---|---|
| 3,656,982 A | 4/1972 | Chapman et al. |
| 4,710,375 A | 12/1987 | Takasuka et al. |
| 2010/0098780 A1 | 4/2010 | Ono et al. |
| 2010/0291014 A1 | 11/2010 | Tellefsen et al. |

FOREIGN PATENT DOCUMENTS

| | | |
|---|---|---|
| EP | 1712596 A2 | 10/2006 |
| JP | 4-66551 A | 3/1992 |
| JP | 2005-213317 A | 8/2005 |

*Primary Examiner* — Deborah D Carr
(74) *Attorney, Agent, or Firm* — Muncy, Geissler, Olds & Lowe, P.C.

(57) ABSTRACT

A metal soap, including metal soap particles in which a fatty acid has from 6 to 22 carbons, and an inorganic crystal nucleating agent with an average particle size of 0.01 to 20 μm absorbed internally into the metal soap particles, wherein the cumulative diameter at 50% of the metal soap particles on a volumetric basis is 1.0 to 30.0 μm, and the internal absorption rate A, represented by formula (1) below, is 30% or greater.

Internal absorption rate $A=100-(X/X')=100$    Formula (1)

X; amount of inorganic crystal nucleating agent contained within metal soap

X'; amount of inorganic crystal nucleating agent contained within pulverized metal soap passed through a 325-mesh filter (wherein X and X' are average values obtained by elemental analysis at three locations in an area of 15 μm square, using a scanning electron microscope/energy dispersive X-ray spectroscopy (SEM/EDX).

5 Claims, No Drawings

METAL SOAP AND MANUFACTURING METHOD THEREFOR

BACKGROUND OF THE INVENTION

1. Field of the Invention

The present invention relates to a metal soap for use in improving the flowability or tactile feel of powders, such as resin powders, granulated urea, and other such organic particles; iron powder, ferrite powder and other such metal particles; or calcium carbonate, colcothar, and other such inorganic particles containing a metal or semimetal, and to a manufacturing method for the same; and relates also to a metal soap with which powders can be imparted with high levels of dispersibility or coating properties, to improve the anti-caking properties, flowability, or tactile feel of the powder, and to a manufacturing method for the same.

2. Description of the Related Art

Metal soaps are used in various fields such as the powder metallurgy field and the cosmetic field. For example, in the powder metallurgy field, due to the need to pour iron powders, ferrite powders, and the like into various molds, high levels of flowability are required of the iron powders and ferrite powders, so metal soaps are used as flow improvers. In the cosmetic field, with regard to powder cosmetics such as powder foundation and face powder, there is a need to improve the tactile feel of the molded product, so a metal soap is dispersed into the main ingredient powder and induced to coat the powder, thereby packing and molding the product into an inner tray or the like. In terms of the effects obtained by improving both anti-caking properties and flowability in powder cosmetics, efforts have been directed to improving the characteristic whereby a given amount of a powder can be picked up smoothly in a friction-free manner (i.e., spreading properties).

Metal soaps are manufactured industrially by a direct method or a double decomposition method. The direct method is a method in which a direct reaction of a fatty acid and a metal oxide or metal hydroxide is brought about, whereas the double decomposition method is a method in which a basic compound is reacted with a fatty acid in the state of an aqueous solution to obtain a basic compound of the fatty acid, which is further reacted with a metal salt containing a metal or semimetal.

In the direct method, there has been proposed, for example, a metal soap manufacturing method in which a fatty acid is dissolved in a heated, mixing-type reactor; a metal oxide or hydroxide containing crystallization water or adsorbed water is added gradually; and at a temperature close to the melting point of the desired metal soap, a reaction is brought about in the absence of solvent, while removing the evolved water. However, the shape of the metal soap obtained thereby is non-uniformly granular, and coarse particles remain, leading to problems such as that the desired dispersibility into and coating properties for the powder are poor (Patent Literature 1).

The double decomposition method, on the other hand, has some advantages, such as little free fatty acid content of the metal soap obtained by the method, and the ability to obtain fine metal soap particles from the reaction. However, in cases in which the particle size of the metal soap is exceedingly fine, a problem arises in that strong intermolecular forces act among the metal soap particles and agglomerating properties become elevated, resulting in a tendency towards poor dispersion during dispersion into or coating of the desired powder (Patent Literature 2).

CITATION LIST

Patent Literature

[PTL 1] Japanese Unexamined Patent Application Publication No. H4-66551 A
[PTL 2] Japanese Unexamined Patent Application Publication No. 2005-213217 A

SUMMARY OF THE INVENTION

Technical Problem

An object of the present invention is to provide a metal soap with which high levels of dispersibility or coating properties can be imparted to a powder, and the anti-caking properties, flowability, or tactile feel of the powder can be improved; and a manufacturing method for the same.

Solution to Problem

As a result of painstaking research in order to solve the aforementioned problem, the inventors discovered that the aforementioned object can be achieved with a metal soap which includes metal soap particles, and an inorganic crystal nucleating agent internally absorbed into the metal soap particles, in which the internal absorption rate of the inorganic crystal nucleating agent falls within a prescribed range.

Specifically, the present invention provides a metal soap including metal soap particles in which the fatty acid has from 6 to 22 carbons, and an inorganic crystal nucleating agent of an average particle size of 0.01 to 20 μm absorbed internally into the metal soap particles, wherein the cumulative diameter at 50% of the metal soap particles on a volumetric basis is 1.0 to 30.0 μm, and the internal absorption rate A, represented by formula (1) below, is 30% or greater.

$$\text{Internal absorption rate } A = 100 - (X'/X) \times 100 \qquad \text{Formula (1)}$$

X; amount of inorganic crystal nucleating agent contained within metal soap

X'; amount of inorganic crystal nucleating agent contained within pulverized metal soap passed through a 325-mesh filter (wherein X and X' are average values obtained by elemental analysis at three locations in an area of 15 μm square, using a scanning electron microscope/energy dispersive X-ray spectroscopy (SEM/EDX), under conditions of an accelerating voltage of 10 kV and a height of 15 mm)

The metal soap of the present invention preferably satisfies a relationship of $B \leq 2.00$, where B denotes a granularity summary value represented by formula (2) below, $C \leq 20$, where C denotes an aggregation degree (%), and E being from 0.810 to 1.000, where E denotes an average circularity of particle groups having particle size at 10% to particle size at 90%, measured by a flow type particle image analyzer.

$$\text{Granularity summary value } B = (D90 - D10)/D50$$
$$(\text{wherein } 1.0 \leq D50 \leq 30.0) \qquad \text{Formula (2)}$$

D10: Cumulative diameter (μm) at 10% of metal soap particles on volumetric basis
D50: Cumulative diameter (μm) at 50% of metal soap particles on volumetric basis
D90: Cumulative diameter (μm) at 90% of metal soap particles on volumetric basis Additionally, in the metal soap of the present invention, it is preferable that the metal soap is a zinc salt or calcium salt, and that the inorganic crystal nucleating agent is one or more selected from the group consisting of silica, zinc oxide, titanium oxide, calcium oxide, boron nitride, talc, mica, synthetic mica, alumina, and sericite.

Further, the present invention provides a method for manufacturing the metal soap of the present invention through reaction, by a double decomposition method, of an inorganic metal salt, and a fatty acid alkali metal salt obtained from a fatty acid having from 6 to 22 carbons, the method including a step of dispersing an inorganic crystal nucleating agent having an average particle size of 0.01 to 20 μm into an aqueous solution of the fatty acid alkali metal salt at a level of 0.1 to 20 mass % with respect to the total amount of the fatty acid and the inorganic crystal nucleating agent to prepare a dispersion solution; and a step of mixing and bringing about a reaction of the dispersion solution and the aqueous solution of the inorganic metal salt.

Advantageous Effects of Invention

According to the metal soap of the present invention, high levels of dispersibility or coating properties can be imparted to a powder, and the anti-caking properties, flowability, or tactile feel of the powder can be improved. Additionally, according to the method for manufacturing the metal soap of the present invention, the metal soap of the present invention can be manufactured consistently, and with good productivity.

DETAILED DESCRIPTION OF THE PREFERRED EMBODIMENTS

An embodiment of the present invention will be explained below.

The metal soap of the present invention can be manufactured, for example, through reaction of a fatty acid alkali metal salt and an inorganic metal salt, by a double decomposition method.

The fatty acid used as the starting material for the fatty acid alkali metal salt may be either the saturated fatty acids or unsaturated fatty acids, and may be either linear or branched. Furthermore, the fatty acid may contain a functional group such as a hydroxyl group, an aldehyde group, or an epoxy group in the structure. Examples of such fatty acids include caproic acid, hepthylic acid, caprylic acid, capric acid, lauric acid, myristic acid, palmitic acid, stearic acid, arachic acid, and behenic acid, with fatty acids having from 7 to 18 carbons being preferred.

When the fatty acid has less than 6 carbons, it may be difficult to obtain the effect of improving anti-caking properties, flowability, or tactile feel of powders, while that having exceeding 22 carbons is difficult to be procured industrially, and the productivity of the metal soap may lower because the solubility of the acid in water is greatly diminished during preparation of the fatty acid alkali metal salt aqueous solution. These fatty acids may be used alone, or two or more types may be used in combination.

As basic compounds for use as the starting material for the fatty acid alkali metal salt includes alkali metal (such as sodium and potassium) hydroxides, and amines such as ammonia, monoethanolamine, diethanolamine, and triethanolamine. It is preferable to use hydroxides of alkali metals such as sodium and potassium (for example, sodium hydroxide or potassium hydroxide), due to their high solubility in water when the fatty acid alkali metal salt has been formed. These basic compounds may be used alone, or two or more types may be used in combination.

The fatty acid alkali metal salt used in the present invention is obtained by reacting a fatty acid and a basic compound, typically at a temperature at or above the melting point of the fatty acid, and at which the fatty acid does not decompose, preferably 100° C. or below, more preferably 50 to 100° C., still more preferably 60 to 95° C., and especially preferably 70 to 95° C.

As the metal soap of the present invention, it is preferable to use a metal soap obtained through a reaction by a double decomposition method in an aqueous solution, of a fatty acid alkali metal salt obtained as above, and an inorganic metal salt containing a metal or semimetal. In other words, the metal soap of the present invention is a salt of a fatty acid and an inorganic metal containing a metal or semimetal.

From the standpoint of improving anti-caking properties, flowability, or tactile feel of poweders, calcium or zinc is preferred for the metal containing a metal or semimetal.

The inorganic metal salt containing a metal or semimetal includes chlorides, sulfates, and nitrates containing a metal or semimetal, and chlorides of calcium, zinc, or the like, sulfates of calcium, zinc, or the like, and nitrates of calcium, zinc, or the like, are particularly preferred due to their high solubility in water, and efficient reaction with fatty acid alkali metal salts. Specifically, there may be cited calcium chloride, calcium acetate, zinc chloride, zinc sulfate, and the like.

The reaction of the fatty acid alkali metal salt and the inorganic metal salt containing a metal or semimetal can be carried out, for example, by separately preparing an aqueous solution of the inorganic metal salt containing a metal or semimetal, and an aqueous solution of the fatty acid alkali metal salt, and then mixing these. For example, the reaction can be carried out by adding the aqueous solution of the inorganic metal salt containing a metal or semimetal to the aqueous solution of the fatty acid alkali metal salt, or by adding both to a separate reaction vessel.

During mixing of the aqueous solution of the fatty acid alkali metal salt and the aqueous solution of the inorganic metal salt containing a metal or semimetal, if, for example, the aqueous solution of the inorganic metal salt containing a metal or semimetal is added all at once to the aqueous solution containing the fatty acid alkali metal salt, there is a risk that the metal soap particles obtained therefrom will have non-uniform shape and a wide granularity distribution. Therefore, in the present invention, it is preferable for the aqueous solution of the inorganic metal salt containing a metal or semimetal to be added gradually dropwise at an appropriate rate to the aqueous solution of the fatty acid alkali metal salt.

In the aforedescribed reaction, it is more preferable to either disperse the inorganic crystal nucleating agent into the prepared aqueous solution of the fatty acid alkali metal salt, and then add the aqueous solution of the inorganic metal salt containing a metal or semimetal, or to add both to a separate reaction vessel.

The inorganic crystal nucleating agent serves as a crystal nuclei for accelerating crystal growth, and has the action of making the crystal size finer or more uniform. By adding the inorganic crystal nucleating agent to the solution of the fatty acid alkali metal salt, when the fatty acid alkali metal salt is uniformly dispersed, and reacted with the aqueous solution of the inorganic metal salt containing a metal or semimetal, the inorganic crystal nucleating agent acts as a nucleating agent during crystal growth of the metal soap particles, so the particle shape originating from the nucleating agent is more uniform, and the granularity distribution of the metal soap particle is sharp.

For the inorganic crystal nucleating agent used in manufacturing the metal soap of the present invention, it is preferable to use a crystal nucleating agent that, during the double decomposition reaction which involves reacting the aqueous solution of the fatty acid alkali metal salt and the aqueous solution of the inorganic metal salt containing a metal or semimetal to induce growth of metal soap particles, does not give rise to melting or compositional change of the inorganic crystal nucleating agent itself; an inorganic crystal nucleating agent containing a metal or semimetal may be used, for example. Specifically, one or more agents selected from the group consisting of silica, zinc oxide, titanium oxide, calcium oxide, boron nitride, talc, mica, synthetic mica, alumina, and sericite can be used.

The average particle size of the inorganic crystal nucleating agent is 0.01 to 20 μm, preferably 0.1 to 20 μm, and more preferably 0.5 to 19 μm. In cases in which the average particle size is less than 0.01 μm, the exceedingly small particle size may result in particles ceasing to function as crystal nuclei, whereas the size greater than 20 μm may lead to a low internal absorption rate A, described later, and to coarser granularity, or non-uniform particle shape, of metal soap particles obtained therewith.

It is noted that the average particle size of the inorganic crystal nucleating agent can be measured by a Microtrac laser diffraction method. The Microtrac laser diffraction method is a method of determining the size by utilizing scattered light obtained by irradiating the particles with a laser beam. In the present invention, measurement can be carried out by a wet method in which a sample is put as-is into a circulated organic solvent in which the inorganic crystal nucleating agent does not dissolve, for example, an organic solvent such as ethanol, or isopropyl alcohol. The particles to be measured in the present invention have an average particle size in a range of 0.1 to 200 μm. The average particle size can be measured, for example, by a Microtrac MT-3000 manufactured by NIKKISO Co., Ltd.

The added amount of the inorganic crystal nucleating agent is normally 0.1 to 20 mass %, preferably 0.5 to 20 mass %, more preferably 1 to 19 mass %, and still more preferably 3 to 18 mass %, with respect to the total amount of the fatty acid and the inorganic crystal nucleating agent. When the added amount of the inorganic crystal nucleating agent is too small, the internal absorption rate A, described later, may be lower, and the granularity of the metal soap particles obtained therewith may become coarser, or the particle shape may be non-uniform. Excessively large added amounts of the inorganic crystal nucleating agent may not produce an effect commensurate to the added amount.

From the standpoint of productivity of the metal soap, and the standpoint of ease of handling of a fatty acid alkali metal salt aqueous solution or of a metal soap slurry obtained therefrom, the concentration of fatty acid alkali metal salt during manufacture of the metal soap is normally 1 to 20 mass %, and preferably 5 to 15 mass %, in aqueous solution. In cases in which the concentration of the fatty acid alkali metal salt is too low, the metal soap productivity may decrease, which is undesirable from a practical standpoint. In cases in which the concentration is too high, the viscosity of the fatty acid alkali metal salt aqueous solution or of a metal soap slurry obtained therefrom rises, and therefore it may be difficult to bring about a uniform reaction.

It is noted that from the standpoint of productivity of the metal soap, and the standpoint of ease of handling of a fatty acid alkali metal salt aqueous solution or of a metal soap slurry obtained therefrom, the concentration of the inorganic metal salt in the inorganic metal salt aqueous solution containing a metal or semimetal is normally 10 to 50 mass %, and preferably 10 to 40 mass %.

The reaction of the fatty acid alkali metal salt and the inorganic metal salt containing a metal or semimetal is carried out under temperature conditions that would be normally employed by a person skilled in the art, in consideration of the solubility of the fatty acid alkali metal salt. The temperature is preferably 50 to 100° C., and more preferably 60 to 95° C. When the reaction temperature is too low, the reaction rate of the fatty acid alkali metal salt and the metal salt containing a metal or semimetal may lower.

With the goal of stabilizing the metal soap slurry to improve the productivity of the metal soap in the reaction process of the fatty acid alkali metal salt and the inorganic metal salt containing a metal or semimetal, it is preferable for a polyalkylene glycol ether, particularly a triblock ether having a structure (EO-PO-EO) in which an oxypropylene block (PO) is sandwiched by oxyethylene blocks (EO), to be present in the metal soap slurry. The amount of polyalkylene glycol ether contained in the metal soap slurry is normally 0.01 to 5 mass %, and preferably 0.05 to 2%, with respect to 100 mass % of the fatty acid alkali metal salt.

It is noted that the polyalkylene glycol ether may be present in the reaction system prior to reacting the basic compound and the fatty acid, or may be present in the reaction system prior to the reaction between the fatty acid alkali metal salt and the inorganic metal salt containing a metal or semimetal.

The metal soap slurry is obtained by the method described above. This metal soap slurry is used as-is, or the solvent therein is separated out by a centrifugal dehydrator, filter press, vacuum rotary filter, or the like, and the material is then washed if needed to remove any byproduct salt containing a metal or semimetal, then dried with a rotary dryer, a flash dryer, a ventilation dryer, a spray dryer, a fluidized bed dryer, or the like. The drying method may be either a continuous or batch type method, and carried out either at normal pressure or under a vacuum. Further, the dried metal soap is pulverized if needed. The pulverization method includes, but is not limited to, a pulverization method by using a pin mill, jet mill, atomizer, or the like. The pulverized metal soap particles are classified. Specifically, an apparatus such as a multi-stage sieve apparatus, in which sieving is carried out by vibrating sieves, is employed to carry out classification and adjust the granularity distribution. The metal soap of the present invention can be obtained in the foregoing manner.

The metal soap of the present invention contains metal soap particles and an inorganic crystal nucleating agent, the inorganic crystal nucleating agent being absorbed into the interior of the metal soap particles. The internal absorption rate A, which indicates the proportion of the inorganic crystal nucleating agent absorbed into the interiors of the metal soap particles, is given by formula (1) below.

Internal absorption rate $A=100-(X/X')\times100$    Formula (1)

X; amount of inorganic crystal nucleating agent contained within metal soap

X'; amount of inorganic crystal nucleating agent contained within pulverized metal soap passed through a 325-mesh filter (wherein X and X' are average values obtained by elemental analysis at three locations in an area of 15 μm square, using a scanning electron microscope/energy dispersive X-ray spectroscopy (SEM/EDX), under conditions of an accelerating voltage of 10 kV and a height of 15 mm)

It is noted that a pulverized metal soap passed through a 325-mesh filter refers to a pulverized product of a metal soap obtained by pulverizing a metal soap and then passing the product through a 325-mesh filter.

In the metal soap of the present invention, the internal absorption rate A is 30% or more, preferably 40% or more, more preferably 50% or more, and even more preferably 60% or more. Where the internal absorption rate A is 30% or more, a higher proportion of the inorganic crystal nucleating agent contributes to the powder characteristics and to the crystal shape of the metal soap produced during the double decomposition reaction, and the prescribed granularity summary value B, aggregation degree C., and average circularity E are easily obtained. On the other hand, where the internal absorption rate A is less than 30%, a lower proportion of the inorganic crystal nucleating agent contributes to the powder characteristics and to the crystal shape of the metal soap produced during the double decomposition reaction, and it may be difficult to obtain the prescribed granularity summary value B, aggregation degree C., and average circularity E.

The cumulative diameter at 50%, on a volumetric basis, of the metal soap particles used in the present invention is 1.0 to 30.0 μm, preferably 5.0 to 25.0 μm, and more preferably 10 to 23.0 μm.

It is preferable for the metal soap particles used in the present invention to have a narrow granularity distribution, because when used in a powder, more uniform coating is possible thereby, and the effect of the present invention can be more consistently expressed with ease.

Specifically, the granularity summary value B, represented by formula (2) below, is preferably such that B≤2.00.

$$\text{Granularity summary value } B=(D90-D10)/D50$$
$$(\text{wherein } 1.0 \leq D50 \leq 30.0) \quad \text{Formula (2)}$$

D10: Cumulative diameter (μm) at 10% of metal soap particles on volumetric basis D50: Cumulative diameter (μm) at 50% of metal soap particles on volumetric basis D90: Cumulative diameter (μm) at 90% of metal soap particles on volumetric basis In the present invention, the granularity summary value B is calculated from the particle sizes measured by a Microtrac laser diffraction method. If the granularity summary value B exceeds 2.00, variability of the particle size of the metal soap particles present during addition to the powder may make it difficult to improve the anti-caking properties, flowability, and tactile feel of the powder.

It is more preferable for the granularity summary value B to satisfy the relationship of 1.00≤B≤2.00. When the relationship of 1.00≤B≤2.00 is satisfied, the effect of the present invention may be obtained more consistently. If the granularity summary value B is below 1.00, it may become difficult to industrially produce the particles, due to a sharp decline in yield, or the like.

It is noted that the granularity summary value B can be adjusted through respective proper adjustment of the concentration of the fatty acid alkali metal salt; the temperature during the reaction of the fatty acid alkali metal salt and the inorganic metal salt containing a metal or semimetal; and the dripping rate at which the metal salt-containing aqueous solution containing a metal or semimetal is dripped into the fatty acid alkali metal salt-containing aqueous solution. Particles having a wide granularity distribution, in other words, a large granularity summary value B, may be adjusted through classification using a sieve, such as a 100-mesh, 200-mesh, or 330-mesh sieve, in a post-process.

The Microtrac laser diffraction method used to determine the granularity summary value B is a method for determining the granularity distribution by utilizing scattered light obtained by irradiating the particles with a laser beam. In the present invention, measurement can be carried out by a wet process in which a sample is put as-is into a circulated organic solvent in which the metal soap particles do not dissolve, for example, an organic solvent such as ethanol or isopropyl alcohol. Additionally, the particles to be measured in the present invention have an average particle size in a range of 0.1 to 200 μm, and the value represented by the above Formula (2) is taken to be the granularity summary value B. It is noted that, in the present invention, the average particle size can be measured, for example, by using a Microtrac MT-3000 manufactured by NIKKISO Co., Ltd.

Further, it is preferable that in the metal soap particles used in the present invention, the aggregation degree C. (%), represented by Formula (3) below satisfies a relationship of C≤20 when measured by a powder tester after the particles have been left to stand for 10 minutes in an 80° C. environment.

$$\text{Aggregation degree } C.=[(\text{mass of fatty acid metal salt particles remaining on a sieve with a mesh size of 350 μm})/2]\times 100\times(1/1)+[(\text{mass of fatty acid metal salt particles remaining on a sieve with a mesh size of 250 μm})/2]\times 100\times(3/5)+[(\text{mass of fatty acid metal salt particles remaining on a sieve with a mesh size of 150 μm})/2]\times 100\times(1/5)]. \quad \text{Formula (3)}$$

The aggregation degree C. (%) is preferably 2≤C≤18, more preferably 2≤C≤15, and even more preferably 2≤C≤13. When the relationship of 2≤C≤13 is satisfied, the effect of the present invention may be obtained more consistently.

It is noted that adjustment of the aggregation degree C. can be carried out by bringing about the reaction of the fatty acid alkali metal salt and the inorganic metal salt containing a metal or semimetal under mild conditions, preventing aggregation of the metal soap particles in the slurry obtained by the reaction. That is, the adjustment may be made by carrying out the reaction between the fatty acid alkali metal salt and the inorganic metal salt at a moderate temperature such that there is no decrease in the reaction rate during the reaction, or by shortening the aging time. Through proper adjustment of these factors during the reaction, the aggregation degree C. can be adjusted to within the range specified in the present invention.

The metal soap particle aggregation degree C. obtained with the powder tester used herein is a value obtained by the following measurement method. Specifically, the following steps (a) to (f) are carried out sequentially using, for example, a powder tester (Model PT-N manufactured by Hosokawa Micron Corporation).

(a) Metal soap particles to be measured are left for 10 minutes in an incubator set to 80° C.

(b) Sieves with mesh sizes of 350 μm, 250 μm, and 150 μm are placed in order from the top onto the shake table of the powder tester.

(c) 2.0 g of the metal soap particles immediately after the step (a) are gently placed on the sieve with a mesh size of 350 μm.

(d) The sieve is shaken for 105 seconds at an amplitude of 1 mm.

(e) The mass of the metal soap particles remaining on each of the sieves is measured.

(f) The masses obtained in the preceding step (e) are sequentially multiplied by weights of 1/1, 3/5, and 1/5, respectively, and these values are then added up, and the value of the percentage calculated in accordance with Formula (3) above is taken as the aggregation degree C. (%).

The above steps (a) to (f) are repeated five times, and the average value thereof is taken as the measured value.

Furthermore, the metal soap particles used in the present invention preferably have a loose bulk density (Da) (g/cc), given by Formula (4) below, such that $0.120 \leq Da \leq 0.200$, and more preferably $0.135 \leq Da \leq 0.180$. With $0.135 \leq Da \leq 0.180$, even higher dispersibility is obtained in instances in which the particles are used in a powder, and the effects of the present invention are more consistently expressed.

The loose bulk density (Da) is a value obtained by the following measurement method. First, using a powder tester (Model PT-N manufactured by Hosokawa Micron Corporation), for example, a sieve having a mesh size of 710 μm is placed on the shaking table, a sample of 250 cc is placed therein and shaken for 30 seconds, and the portion of the sample that has fallen into a measuring cup placed under the sieve is collected. After scraping away excess metal soap particles above the cup using the supplied blade, the mass of the cup containing the sample inside is measured. It is noted that, in the present invention, this procedure and measurements are repeated five times, and the average value thereof is taken as the measured value of the bulk density (Da). The Model PT-N automatically displays the measured values.

Loose bulk density (Da) (g/cc)=mass of cup containing sample (g)/volume of cup (cc)   Formula (4)

When the metal soap particles used in the present invention are measured with a flow type particle image analyzer, an average circularity E of particle groups having particle size at 10% to particle size at 90% (hereinafter termed simply "average circularity E") is preferably 0.810 to 1.000, more preferably 0.820 to 0.950, and even more preferably 0.820 to 0.920. When the average circularity E is within the above range, in instances of use of the particles in a powder, the dispersibility and coating properties can be further enhanced, and the effects of the present invention can be more consistently expressed with ease.

It is noted that adjustment of the average circularity E can be carried out by bringing about under mild conditions the reaction of the fatty acid alkali metal salt and the inorganic metal salt, thus preventing the particle shape of the metal soap particles in the slurry obtained by the reaction from becoming non-uniform. That is, adjustments can made, for example, by carrying out the reaction at a mild temperature such that there is no decline in the reaction rate during the reaction of the fatty acid alkali metal salt and the inorganic metal salt, by moderating the drip rate at which the metal salt-containing aqueous solution is dripped into the fatty acid alkali metal salt-containing aqueous solution, or by adding the polyalkylene glycol ether mentioned previously in order to stabilize the slurry. By properly adjusting these factors during the reaction, the average circularity E may be adjusted to within the range specified in the present invention. It is further preferable that the inorganic metal salt aqueous solution containing a metal or semimetal is added subsequent to dispersion of the inorganic crystal nucleating agent having an average particle size of 0.01 to 20 μm into the prepared fatty acid alkali metal salt-containing aqueous solution at a level of 0.1 to 20 mass % with respect to the fatty acid alkali metal salt aqueous solution; or both solutions are added to a separate reaction vessel. When the reaction with the inorganic metal salt aqueous solution containing a metal or semimetal is brought about after the crystal nucleating agent has been dispersed in the fatty acid alkali metal salt-containing aqueous solution, metal soap particles seeded by nuclei of the crystal nucleating agent are formed, and therefore it is easy to grow the particles to uniform shape, and to obtain a high degree of circularity.

The average circularity E in the present invention is used as a simple method for quantitatively representing the shape of the metal soap particles, and may be defined as follows. First, for example, a flow type particle image analyzer "FPIA-3000" made by Sysmex Corporation is used to measure particles having equivalent circular diameter within a range of 0.5 to 200 μm, and then the circularity (ai) of each of the measured particles is calculated from the following Formula (5).

Circularity (ai)=(circumference of a circle having the same area as a projected image of a particle)/ (circumference of the particle projected image)   Formula (5)

The average circularity E in the present invention is an index which indicates the degree of irregularity of the metal soap particle shape; as the surface shape of a metal soap particle approaches circularity, the value approaches 1.000, whereas a more complex surface shape of a particle will have a smaller average circularity value. The "FPIA-3000," which is one of the measuring devices that can be used in the present invention, employs a calculation method in which the circularity of each particle is calculated, and on the basis of the circularity obtained thereby, a particle circularity range of 0.4 to 1.0 is divided into classes of 61 segments, and the center and frequency of the segmentation points are used to calculate the average circularity.

In the present invention, the sum of circularity values of the particles within the range of particle size at 10% to particle size at 90%, counting from the small-particle size end of the particle size distribution, from among all of the particles measured by the above-described measuring device is divided by the number of particles to give the average circularity E of particle groups having particle size at 10% to particle size at 90%.

The average circularity E of particle groups having particle size at 10% to particle size at 90% is measured as follows, for example. 30 ml of deionized water from which solid impurities and the like have been removed in advance is placed in a vessel, and after adding a surfactant, preferably a polyoxyethylene nonylphenyl ether (trade name: Nonion NS-210 manufactured by NOF Corporation), as a dispersant, 20 mg of a measurement sample is further added and uniformly dispersed therein. As the dispersing means, there may be employed, for example, an ultrasonic disperser Model UH-50 (manufactured by SMT Corporation, 20 kHz, 50 W) equipped with a titanium alloy tip having the diameter of 5 mm as an oscillator, to carry out a five-minute dispersion process to prepare a dispersion solution for measurement having a dispersion concentration of 3,000 particles/ml to 20,000 particles/ml. During this time, the dispersion solution for measurement is appropriately cooled so that the temperature does not go above 40° C. or higher. Subsequently, the flow type particle image analyzer "FPIA-3000" is used to carry out measurement, and the obtained data is processed to obtain the average circularity E.

EXAMPLES

The present invention will be described in more specific terms below by citing Examples and Comparative Examples.

Synthesis Example 1

250 g of hepthylic acid and 1880 g of water were placed in a 3 L separable flask, and heated to 80° C. Next, 160.0 g of a 48 mass % sodium hydroxide aqueous solution was added thereto, and then the mixture was stirred for one hour at the same temperature (80° C.), to obtain a fatty acid alkali metal salt aqueous solution. 12 g of silica having an average particle size of 2.9 μm was added thereto, followed by stirring for one hour. Subsequently, with the solution held at 80° C., 392.6 g of a 25 mass % zinc chloride aqueous solution was added dropwise to the fatty acid alkali metal salt aqueous solution over a 40-minute period. After completion of the dropwise addition, the solution was stirred for 10 minutes and aged while being held at 80° C. 1500 g of water was added to the fatty acid zinc salt aqueous solution slurry obtained thereby, followed by cooling to 65° C. or below. The material was then filtered with a suction filter, washed twice with 1000 g of water, and the cake obtained thereby was dried and pulverized by a micron dryer, to obtain fatty acid zinc salt particles.

Synthesis Example 2

250 g of capric acid and 1927 g of water were placed in a 3 L separable flask, and heated to 80° C. Next, 120.9 g of a 48 mass % sodium hydroxide aqueous solution was added thereto, and then the mixture was stirred for one hour at the same temperature (80° C.), to obtain a fatty acid alkali metal salt aqueous solution. 4.6 g of zinc oxide having an average particle size of 0.9 μm was added thereto, followed by stirring for one hour. Subsequently, with the solution held at 80° C., 241.6 g of a 35 mass % calcium chloride aqueous solution was added dropwise to the fatty acid alkali metal salt aqueous solution over a 30-minute period. After completion of the dropwise addition, the solution was stirred for 30 minutes and aged while being held at 80° C. 1500 g of water was added to the fatty acid calcium salt aqueous solution slurry obtained thereby, followed by cooling to 65° C. or below. The material was then filtered with a suction filter, washed twice with 1000 g of water, and the cake obtained thereby was dried and pulverized by a micron dryer, to obtain fatty acid calcium salt particles.

Synthesis Example 3

250 g of caproic acid, 1.25 g of polyethylene glycol-polypropylene glycol block ether (trade name: Plonon #104 manufactured by NOF Corporation), and 1868 g of water were placed in a 3 L separable flask, and heated to 90° C. Next, 179.4 g of a 48 mass % sodium hydroxide aqueous solution was added thereto, and then the mixture was stirred for one hour at the same temperature (90° C.), to obtain a fatty acid alkali metal salt aqueous solution. 15 g of calcium hydroxide having an average particle size of 16.7 μm was added thereto, followed by stirring for one hour. Subsequently, with the solution held at 90° C., 440.2 g of a 25 mass % zinc chloride aqueous solution was added dropwise to the fatty acid alkali metal salt aqueous solution over a 30-minute period. After completion of the dropwise addition, the solution was stirred for 10 minutes and aged while being held at 90° C. 1500 g of water was added to the fatty acid zinc salt aqueous solution slurry obtained thereby, followed by cooling to 65° C. or below. The material was then filtered with a suction filter, washed twice with 1000 g of water, and the cake obtained thereby was dried and pulverized by a micron dryer, to obtain fatty acid zinc salt particles.

Synthesis Example 4

250 g of hepthylic acid, 1.25 g of polyethylene glycol-polypropylene glycol block ether (trade name: Plonon #104 manufactured by NOF Corporation), and 1888 g of water were placed in a 3 L separable flask, and heated to 90° C. Next, 160.0 g of a 48 mass % sodium hydroxide aqueous solution was added thereto, and then the mixture was stirred for one hour at the same temperature (90° C.), to obtain a fatty acid alkali metal salt aqueous solution. 10 g of boron nitride having an average particle size of 18.4 μm was added thereto, followed by stirring for one hour. Subsequently, with the solution held at 90° C., 392.6 g of a 25 mass % zinc chloride aqueous solution was added dropwise to the fatty acid alkali metal salt aqueous solution over a 40-minute period. After completion of the dropwise addition, the solution was stirred for 10 minutes and aged while being held at 90° C. 1500 g of water was added to the fatty acid zinc salt aqueous solution slurry obtained thereby, followed by cooling to 65° C. or below. The material was then filtered with a suction filter, washed twice with 1000 g of water, and the cake obtained thereby was dried and pulverized by a micron dryer, to obtain fatty acid zinc salt particles.

Synthesis Example 5

250 g of lauric acid, 1.25 g of polyethylene glycol-polypropylene glycol block ether (trade name: Plonon #104 manufactured by NOF Corporation), and 1944 g of water were placed in a 3 L separable flask, and heated to 90° C. Next, 104.0 g of a 48 mass % sodium hydroxide aqueous solution was added thereto, and then the mixture was stirred for one hour at the same temperature (90° C.), to obtain a fatty acid alkali metal salt aqueous solution. 20 g of talc having an average particle size of 10.2 μm was added thereto, followed by stirring for one hour. Subsequently, with the solution held at 90° C., 207.8 g of a 35 mass % calcium chloride aqueous solution was added dropwise to the fatty acid alkali metal salt aqueous solution over a 30-minute period. After completion of the dropwise addition, the solution was stirred for 10 minutes and aged while being held at 90° C. 1500 g of water was added to the fatty acid calcium salt aqueous solution slurry obtained thereby, followed by cooling to 65° C. or below. The material was then filtered with a suction filter, washed twice with 1000 g of water, and the cake obtained thereby was dried and pulverized by a micron dryer, to obtain fatty acid calcium salt particles.

Synthesis Example 6

250 g of myristic acid, 1.25 g of polyethylene glycol-polypropylene glycol block ether (trade name: Plonon #104 manufactured by NOF Corporation), and 1957 g of water were placed in a 3 L separable flask, and heated to 90° C. Next, 91.2 g of a 48 mass % sodium hydroxide aqueous solution was added thereto, and then the mixture was stirred for one hour at the same temperature (90° C.), to obtain a fatty acid alkali metal salt aqueous solution. 30 g of mica having an average particle size of 16.2 μm was added thereto, followed by stirring for one hour. Subsequently, with the solution held at 90° C., 223.8 g of a 25 mass % zinc chloride aqueous solution was added dropwise to the fatty acid alkali metal salt aqueous solution over a 40-minute period. After completion of the dropwise addition, the solution was stirred for 10 minutes and aged while being held at 90° C. 1500 g of water was added to the fatty acid zinc salt aqueous solution slurry obtained thereby, followed by cooling to 65° C. or below. The material was then filtered with a suction filter, washed twice with 1000 g of water, and the cake obtained thereby was dried and pulverized by a micron dryer, to obtain fatty acid zinc salt particles.

Synthesis Example 7

250 g of stearic acid, 1.25 g of polyethylene glycol-polypropylene glycol block ether (trade name: Plonon #104 manufactured by NOF Corporation), and 1973 g of water were placed in a 3 L separable flask, and heated to 90° C. Next, 73.2 g of a 48 mass % sodium hydroxide aqueous solution was added thereto, and then the mixture was stirred for one hour at the same temperature (90° C.), to obtain a fatty acid alkali metal salt aqueous solution. 50 g of alumina having an average particle size of 0.7 μm was added thereto, followed by stirring for one hour. Subsequently, with the solution held at 90° C., 179.7 g of a 25 mass % zinc chloride aqueous solution was added dropwise to the fatty acid alkali metal salt aqueous solution over a 40-minute period. After completion of the dropwise addition, the solution was stirred for 10 minutes and aged while being held at 90° C. 1500 g of water was added to the fatty acid zinc salt aqueous solution slurry obtained thereby, followed by cooling to 65° C. or below. The material was then filtered with a suction filter, washed twice with 1000 g of water, and the cake obtained thereby was dried and pulverized by a micron dryer, to obtain fatty acid zinc salt particles.

Synthesis Example 8

250 g of stearic acid, 1.25 g of polyethylene glycol-polypropylene glycol block ether (trade name: Plonon #104 manufactured by NOF Corporation), and 1973 g of water were placed in a 3 L separable flask, and heated to 90° C. Next, 73.2 g of a 48 mass % sodium hydroxide aqueous solution was added thereto, and then the mixture was stirred for one hour at the same temperature (90° C.), to obtain a fatty acid alkali metal salt aqueous solution. 6.4 g of sericite having an average particle size of 9.4 μm was added thereto, followed by stirring for one hour. Subsequently, with the solution held at 90° C., 179.7 g of a 25 mass % zinc chloride aqueous solution was added dropwise to the fatty acid alkali metal salt aqueous solution over a 40-minute period. After completion of the dropwise addition, the solution was stirred for 10 minutes and aged while being held at 90° C. 1500 g of water was added to the fatty acid zinc salt aqueous solution slurry obtained thereby, followed by cooling to 65° C. or below. The material was then filtered with a suction filter, washed twice with 1000 g of water, and the cake obtained thereby was dried and pulverized by a micron dryer, to obtain fatty acid zinc salt particles.

Comparative Compound 1

Zinc stearate (trade name "Zinc Stearate GF-200", manufactured by NOF Corporation)

Comparative Compound 2

Zinc laurate (trade name "Powder Base L", manufactured by NOF Corporation)

Comparative Compound 3

Calcium stearate (trade name "Calcium Stearate", manufactured by NOF Corporation)

Comparative Compound 4

Zinc stearate (trade name "Nissan Elector MZ-2", manufactured by NOF Corporation)

Synthesis Example 9

250 g of hepthylic acid, 1.25 g of polyethylene glycol-polypropylene glycol block ether (trade name: Plonon #104 manufactured by NOF Corporation), and 1888 g of water were placed in a 3 L separable flask, and heated to 90° C. Next, 160.0 g of a 48 mass% sodium hydroxide aqueous solution was added thereto, and then the mixture was stirred for one hour at the same temperature (90° C.), to obtain a fatty acid alkali metal salt aqueous solution. 97.2 g of mica having an average particle size of 16.2 μm was added thereto, followed by stirring for one hour. Subsequently, with the solution held at 90° C., 392.6 g of a 25 mass % zinc chloride aqueous solution was added dropwise to the fatty acid alkali metal salt aqueous solution over a 30-minute period. After completion of the dropwise addition, the solution was stirred for 10 minutes and aged while being held at 90° C. 1500 g of water was added to the fatty acid zinc salt aqueous solution slurry obtained thereby, followed by cooling to 65° C. or below. The material was then filtered with a suction filter, washed twice with 1000 g of water, and the cake obtained thereby was dried and pulverized by a micron dryer, to obtain fatty acid zinc salt particles.

Examples 1 to 8, Comparative Examples 1 to 5

Measurement of Physical Properties of Fatty Acid Metal Salt Particle

Synthesis Examples 1 to 9 and Comparative Compounds 1 to 4 were measured to determine D10, D50, D90, the granularity summary value B, the loose bulk density (Da), the average circularity E, and the aggregation degree C. (%), respectively, according to the methods described herein.

It is noted that D10, D50, D90, and the granularity summary value B were measured with a Microtrac MT-3000 manufactured by NIKKISO Co., Ltd; the loose bulk density (Da) and the aggregation degree C. (%) with a powder tester (model PT-N manufactured by Hosokawa Micron Corporation; and the average circularity E with a flow type particle image analyzer "FPIA-3000" manufactured by Sysmex Corporation, respectively. Further, the internal absorption rate A for Synthesis Examples 1 to 9 was measured according to the methods described herein. The measurement results are tabulated in Table 1.

Examples 1 to 8, Comparative Examples 1 to 5

Evaluation of Metal Soap Particles

Using the fatty acid metal salt particles of Synthesis Examples 1 to 9 and Comparative Compounds 1 to 4 as the metal soap, the soaps were mixed with a powder, and the angle of repose, bulk specific gravity (packed density), and fall velocity were measured as described below.

JIP-300A-120 iron powder made by JFE Steel Corp. (atomized iron power (sprayed iron powder), average particle size 74 μm) was used as the powder. Particles of the metal soaps (fatty acid salts) of the Examples and Comparative Examples were respectively added (internally added) in amounts of 0.4 mass % to the iron powder, and mixed for 15 minutes at a vibration velocity of 60 rpm in a rocking mill (made by Seiwa Giken Co.,Ltd.) to obtain samples for evaluation. The results are shown in Tables 2 and 3.

(Repose angle)

The angle of repose was measured by using an "AOD powder characteristics measuring device" manufactured by Tsutsui Scientific Instruments Co., Ltd. The number of measurements was N=5, the average of which was taken as the angle of repose value. The unit is degrees (°).

(Bulk specific gravity (packed density))

The bulk specific gravity was measured in accordance with JIS K6721-1995, using a bulk specific gravity meter model A manufactured by Kyowa Rika Kogyo K.K. The number of measurements was N=5, the average of which was taken as the bulk specific gravity value. The unit is g/cc.

(Fall velocity)

The fall velocity was measured using the Ford cup stipulated by JIS K5402-1995. The number of measurements was N=5, the average of which was taken as the fall velocity value. The unit is seconds.

TABLE 1

| | | Fatty acid metal salt type | Crystal nucleating agent containing metal or semimetal Particle size, Added amount | Measurement result | | | | | | | |
|---|---|---|---|---|---|---|---|---|---|---|---|
| | | | | Internal absorption rate A (%) | D10 (μm) | D50 (μm) | D90 (μm) | Granularity Summary value B | Loose bulk Density Da (g/cc) | Average Circularity E | Aggregation degree C (%) |
| Ex. 1 | Synthesis Ex. 1 | Zn salt | Silica 2.9 μm, 4.6 mass % | 48.1 | 7.12 | 19.7 | 32.1 | 1.27 | 0.145 | 0.828 | 10.7 |
| Ex. 2 | Synthesis Ex. 2 | Ca salt | Zinc oxide 0.9 μm, 1.8 mass % | 62.8 | 7.94 | 19.1 | 38.7 | 1.61 | 0.169 | 0.822 | 6.2 |
| Ex. 3 | Synthesis Ex. 3 | Zn salt | Calcium hydroxide 16.7 μm, 5.7 mass % | 32.4 | 7.12 | 18.6 | 39.5 | 1.74 | 0.171 | 0.834 | 15.7 |
| Ex. 4 | Synthesis Ex. 4 | Zn salt | Boron nitride 18.4 μm, 3.8 mass % | 35.2 | 5.53 | 6.65 | 17.6 | 1.82 | 0.178 | 0.893 | 8.2 |
| Ex. 5 | Synthesis Ex. 5 | Ca salt | Talc 10.2 μm, 7.4 mass % | 42.9 | 7.95 | 19.5 | 38.6 | 1.57 | 0.136 | 0.867 | 17.2 |
| Ex. 6 | Synthesis Ex. 6 | Zn salt | Mica 16.2 μm, 10.7 mass % | 33.8 | 6.12 | 20.9 | 42.6 | 1.75 | 0.141 | 0.821 | 13.2 |
| Ex. 7 | Synthesis Ex. 7 | Zn salt | Alumina 0.7 μm, 16.7 mass % | 42.5 | 2.17 | 7.25 | 12.6 | 1.44 | 0.138 | 0.882 | 3.8 |
| Ex. 8 | Synthesis Ex. 8 | Zn salt | Sericite 9.4 μm, 2.5 mass % | 31.5 | 7.45 | 17.8 | 35.6 | 1.58 | 0.133 | 0.834 | 15.6 |
| Com. Ex. 1 | Com. Compound 1 | Zn salt | Not added | — | 8.39 | 20.7 | 39.5 | 3.81 | 0.250 | 0.755 | 23.3 |
| Com. Ex. 2 | Com. Compound 2 | Zn salt | Not added | — | 2.60 | 6.60 | 14.2 | 2.17 | 0.171 | 0.806 | 14.2 |
| Com. Ex. 3 | Com. Compound 3 | Ca salt | Not added | — | 2.52 | 9.66 | 39.6 | 3.84 | 0.182 | 0.781 | 35.4 |
| Com. Ex. 4 | Com. Compound 4 | Zn salt | Not added | — | 1.30 | 3.28 | 6.27 | 1.51 | 0.108 | 0.909 | 81.4 |
| Com. Ex. 5 | Synthesis Ex. 9 | Zn salt | Mica 16.2 μm, 28.0 mass % | 21.7 | 6.41 | 23.6 | 62.8 | 2.39 | 0.142 | 0.823 | 31.8 |

TABLE 2

| | Ex. | | | | | | | |
|---|---|---|---|---|---|---|---|---|
| | 1 Synthesis Ex. 1 | 2 Synthesis Ex. 2 | 3 Synthesis Ex. 3 | 4 Synthesis Ex. 4 | 5 Synthesis Ex. 5 | 6 Synthesis Ex. 6 | 7 Synthesis Ex. 7 | 8 Synthesis Ex. 8 |
| Repose angle (°) | 35.1 | 34.2 | 34.6 | 35.4 | 35.9 | 34.0 | 33.8 | 34.2 |
| Bulk specific gravity (g/cc) | 3.45 | 3.48 | 3.41 | 3.38 | 3.39 | 3.47 | 3.51 | 3.48 |
| Powder flowability (sec) | 11.3 | 11.1 | 11.6 | 11.9 | 11.5 | 11.3 | 10.9 | 11.6 |

TABLE 3

| | Com. Ex.s | | | | |
|---|---|---|---|---|---|
| | 1 Com. Compound 1 | 2 Com. Compound 2 | 3 Com. Compound 3 | 4 Com. Compound 4 | 5 Synthesis Ex. 9 |
| Repose angle (°) | 39.3 | 36.9 | 37.2 | 36.1 | 37.8 |
| Bulk specific gravity (g/cc) | 3.11 | 3.24 | 3.18 | 3.36 | 3.27 |
| Powder flow/ability (sec) | 13.2 | 12.4 | 12.8 | 12.0 | 12.5 |

From the low values of angle of repose in Examples 1 to 8, it may be appreciated that the flowability of the powder is high, and extremely high flowability can be imparted to the atomized iron powder. Additionally, it may be appreciated that the bulk specific gravity values are high, and packability is excellent.

In contrast to this, the metal soap particles of Comparative Examples 1 and 2 are large, and the particles shapes are irregular, leading to unevenness and poor dispersibility when dispersed. In Comparative Examples 3 and 4, the aggregation degree is high, and dispersibility is poor. In Comparative Example 5, due to the large amount of the inorganic crystal nucleating agent, the inorganic crystal nucleating agent becomes oversaturated within the reaction system, the internal absorption rate A declines, and granularity is irregular, leading to poor dispersibility.

Examples 9 to 16, Comparative Examples 6 to 10

Evaluation of Metal Soap Particles

The fatty acid metal salt particles of Synthesis Examples 1 to 9 and Comparative Compounds 1 to 4 were used as a metal soap to prepare the solid powder cosmetics, specifically, powder foundation, of the compositions shown in Table 4, and the cosmetics were packed into inner trays, and evaluated as to spreading properties by the method described below.

TABLE 4

| Formulation | Added amount (mass %) |
|---|---|
| Metal soap (Synthesis Ex.s 1 to 9, Com. Compounds 1 to 4) | 15 |
| Nylon powder | 30 |
| Mica | 30 |
| Red iron oxide (colcothar) | 4 |
| Yellow iron oxide | 8 |
| Black iron oxide | 3 |

TABLE 4-continued

| Formulation | Added amount (mass %) |
|---|---|
| Squalane | 5 |
| Dimethylpolysiloxane | 1 |
| Octyldodecyl myristate | 2 |
| Sorbitan sesquioleate | 1.7 |
| Propylparaben | 0.2 |
| Fragrance | 0.1 |

Spreading properties 20 female panelists (aged 20 to 35) were asked to make a determination in the following manner as to the spreadability (spreading properties) when they used the solid powder cosmetics; average values for the 20 panelists were calculated, and the results are shown in Tables 5 and 6. Solid powder cosmetics for which the average value was 1.5 points or above were evaluated as being cosmetics having good tactile feel.

2 points; spreadability during use was felt to be good
1 point; spreadability during use was felt to be somewhat poor
0 points; spreadability during use was felt to be poor

TABLE 5

| | Ex. | | | | | | | |
|---|---|---|---|---|---|---|---|---|
| | 9 Synthesis Ex. 1 | 10 Synthesis Ex. 2 | 11 Synthesis Ex. 3 | 12 Synthesis Ex. 4 | 13 Synthesis Ex. 5 | 14 Synthesis Ex. 6 | 15 Synthesis Ex. 7 | 16 Synthesis Ex. 8 |
| Spreading properties | 1.9 | 1.8 | 1.9 | 1.9 | 1.8 | 1.9 | 1.8 | 1.8 |

TABLE 6

| | Com. Ex.s | | | | |
|---|---|---|---|---|---|
| | 6 Com. Compound 1 | 7 Com. Compound 2 | 8 Com. Compound 3 | 9 Com. Compound 4 | 10 Synthesis Ex. 9 |
| Spreading properties | 1.2 | 1.3 | 1.1 | 1.2 | 1.4 |

The results obtained showed that solid powder cosmetics employing the fatty acid metal salt particles of the present invention in Examples 9 to 16 all had good spreading properties, and good tactile feel.

In Comparative Examples 6 to 10, on the other hand, adequate performance is not obtained. That is, due to the fact that the metal soap particles which are a component of the present invention are not blended in the formulations of Comparative Examples 6 to 9, the spreading properties of each are poor, and tactile feel is not good. Comparative Example 10, due to the large amount of the inorganic crystal nucleating agent, the inorganic crystal nucleating agent becomes oversaturated within the reaction system, the internal absorption rate A declines, and granularity is irregular, thus leading to poor spreading properties, and tactile feel that is not good.

INDUSTRIAL APPLICABILITY

The anti-caking properties, flowability, and tactile feel of powders can be improved by mixing the metal soap of the present invention with powders such as resin powders, granulated urea, and other such organic particles; iron powder, ferrite powder and other such metal particles; or calcium carbonate, colcothar, and other such inorganic particles containing a metal or semimetal.

RELATED APPLICATIONS

The present application claims priority on the basis of Japanese Patent Application filed on Feb. 17, 2015 (Japanese Patent Application No. 2015-28558), the entire contents of which are incorporated herein by reference.

What is claimed is:

1. A metal soap, comprising metal soap particles in which a fatty acid has from 6 to 22 carbons, and an inorganic crystal nucleating agent with an average particle size of 0.01 to 20 μm absorbed internally into the metal soap particles, wherein the cumulative diameter at 50% of the metal soap particles on a volumetric basis is 1.0 to 30.0μm, and the internal absorption rate A, represented by formula (1) below, is 30% or greater:

Internal absorption rate $A=100-(X/X')\times 100$  Formula (1)

X; amount of inorganic crystal nucleating agent contained within metal soap,

X'; amount of inorganic crystal nucleating agent contained within pulverized metal soap passed through a 325-mesh filter wherein X and X' are average values obtained by elemental analysis at three locations in an area of 15 μm square, using a scanning electron microscope/energy dispersive X-ray spectroscopy (SEM/EDX), under conditions of an accelerating voltage of 10 kV and a height of 15 mm.

2. The metal soap according to claim 1, wherein the metal soap satisfies a relationship of B <2.00, where B denotes a granularity summary value represented by formula (2) below, C <20, where (C) denotes an aggregation degree (%), and E being from 0.810 to 1.000, where E denotes an average circularity of particle groups having particle size at 10% to particle size at 90%, measured by a flow type particle image analyzer:

Granularity summary value $B=(D90-D10)/D50$
(wherein $1.0 < D50 < 30.0$)  Formula (2)

D10: Cumulative diameter (μm) at 10% of metal soap particles on volumetric basis, D50: Cumulative diameter (μm) at 50% of metal soap particles on volumetric basis, D90: Cumulative diameter (μm) at 90% of metal soap particles on volumetric basis.

3. The metal soap according to claim 1, wherein the metal soap is a zinc salt or a calcium salt.

4. The metal soap according to claim 1, wherein the inorganic crystal nucleating agent is one or more agents selected from the group consisting of silica, zinc oxide, titanium oxide, calcium oxide, boron nitride, talc, mica, synthetic mica, alumina, and sericite.

5. A method for manufacturing the metal soap according to claim 1 through reaction, by a double decomposition method, of an inorganic metal salt, and a fatty acid alkali metal salt obtained from a fatty acid having from 6 to 22 carbons, the method comprising:

a step of dispersing an inorganic crystal nucleating agent having an average particle size of 0.01 to 20 μm into an aqueous solution of the fatty acid alkali metal salt at a level of 0.1 to 20 mass % with respect to the total amount of the fatty acid and the inorganic crystal nucleating agent to prepare a dispersion solution; and a step of mixing and bringing about a reaction of the dispersion solution and the aqueous solution of the inorganic metal salt.

* * * * *